US00PP31443P2

(12) United States Plant Patent
Wyles

(10) Patent No.: US PP31,443 P2
(45) Date of Patent: Feb. 18, 2020

(54) APPLE TREE NAMED 'TEMPTATION'

(50) Latin Name: ***Malus domestica* Borkh**
Varietal Denomination: Temptation

(71) Applicant: Foxtrot Apples, LLC, Tieton, WA (US)

(72) Inventor: Robert Wyles, Tieton, WA (US)

(73) Assignee: Foxtrot Apples, LLC, Tieton, WA (US)

( * ) Notice: Subject to any disclaimer, the term of this patent is extended or adjusted under 35 U.S.C. 154(b) by 0 days.

(21) Appl. No.: 15/999,981

(22) Filed: Sep. 7, 2018

(51) Int. Cl.
*A01H 5/08* (2018.01)
*A01H 6/74* (2018.01)

(52) U.S. Cl.
USPC ..... Plt./162
CPC ..... *A01H 6/7418* (2018.05)

(58) Field of Classification Search
USPC ..... Plt./161, 162
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Temptation' is a 'Gala'-type apple variety. It was first selected for its intense red fruit. It is distinguished from its parent 'Foxtrot' and other Gala-type varieties by its large, intense red early-maturing fruit and its exceptional flavor.

5 Drawing Sheets

Latin name: *Malus domestica* Borkh.
Variety denomination: 'Temptation'.

BACKGROUND OF THE VARIETY

'Temptation' is a new and distinct variety of 'Gala'-type apple tree *Malus domestica* Borkh. The new variety is believed to be a naturally-occurring whole-tree mutation of 'Foxtrot' (U.S. Plant Pat. No. 24,664), and is characterized by its large, intense red early-maturing fruit.

'Temptation' was first observed in a commercial orchard planted with 'Foxtrot' trees near Basin City, Wash. in 2013. After a season of observation, the variety was asexually reproduced by budding in 2014 at Basin City, Tieton, and Connell, Wash. to determine whether the desirable characteristics of fruit size, intense skin color and early maturity would carry through to subsequent generations. 'Temptation' has been observed to remain true to type over successive asexually propagated generations.

BRIEF DESCRIPTION OF THE VARIETY

'Temptation' is a 'Gala'-type apple variety. It was first selected for its intense red fruit. It is distinguished from 'Foxtrot', 'Tenroy Gala' (U.S. Plant Pat. No. 4,121) and other Gala-type varieties by its intense red early-maturing fruit and exceptional flavor. 'Temptation' is further distinguished from 'Foxtrot' by its later bloom time (two days after 'Foxtrot') and earlier harvest maturity (three to five days before 'Foxtrot').

BRIEF DESCRIPTION OF THE PHOTOGRAPHS

Figure 1:
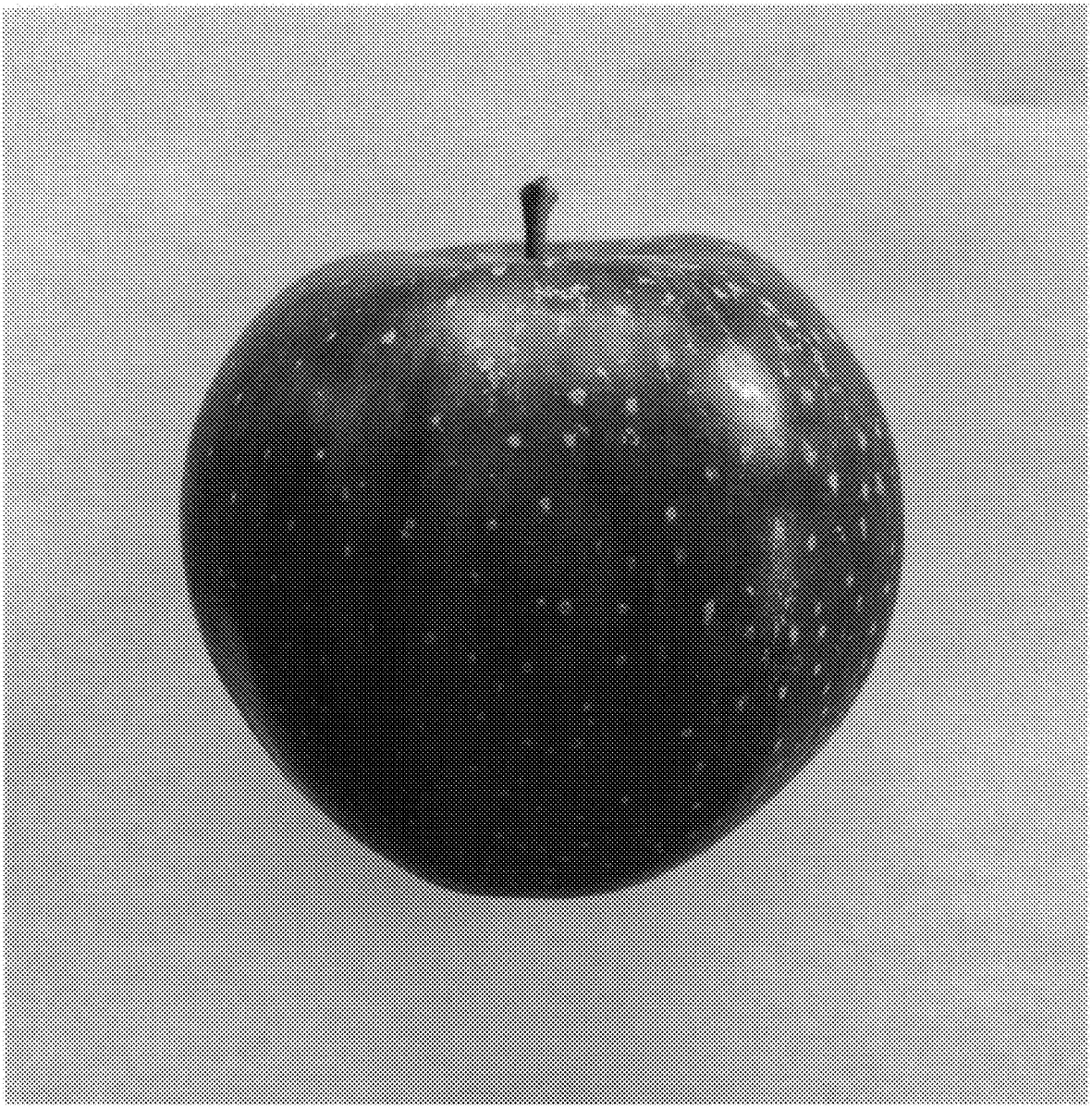
Figure 2:
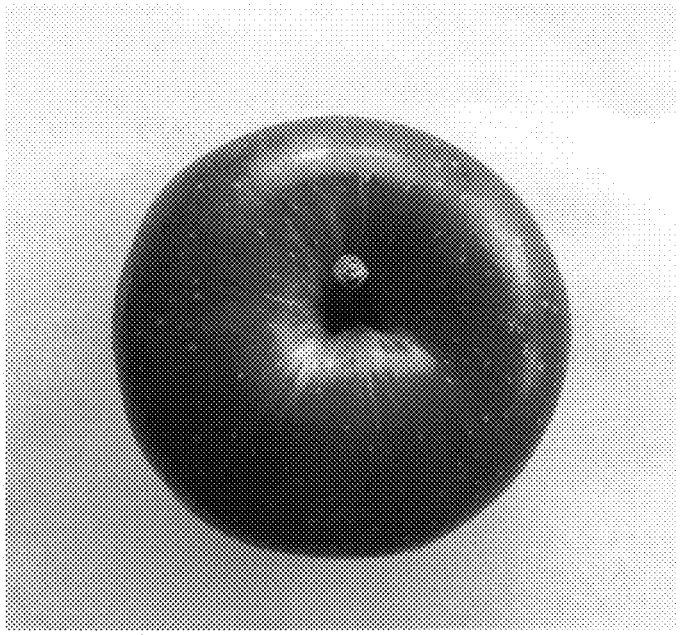
Figure 3:
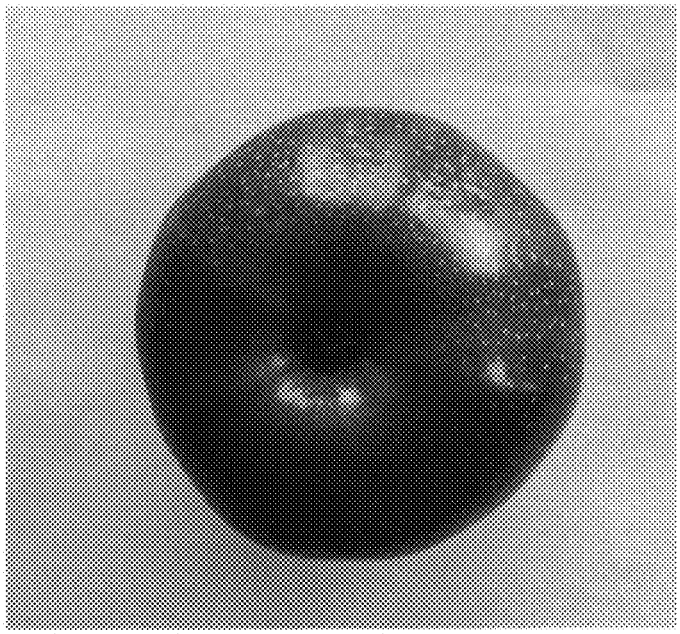
Figure 4:
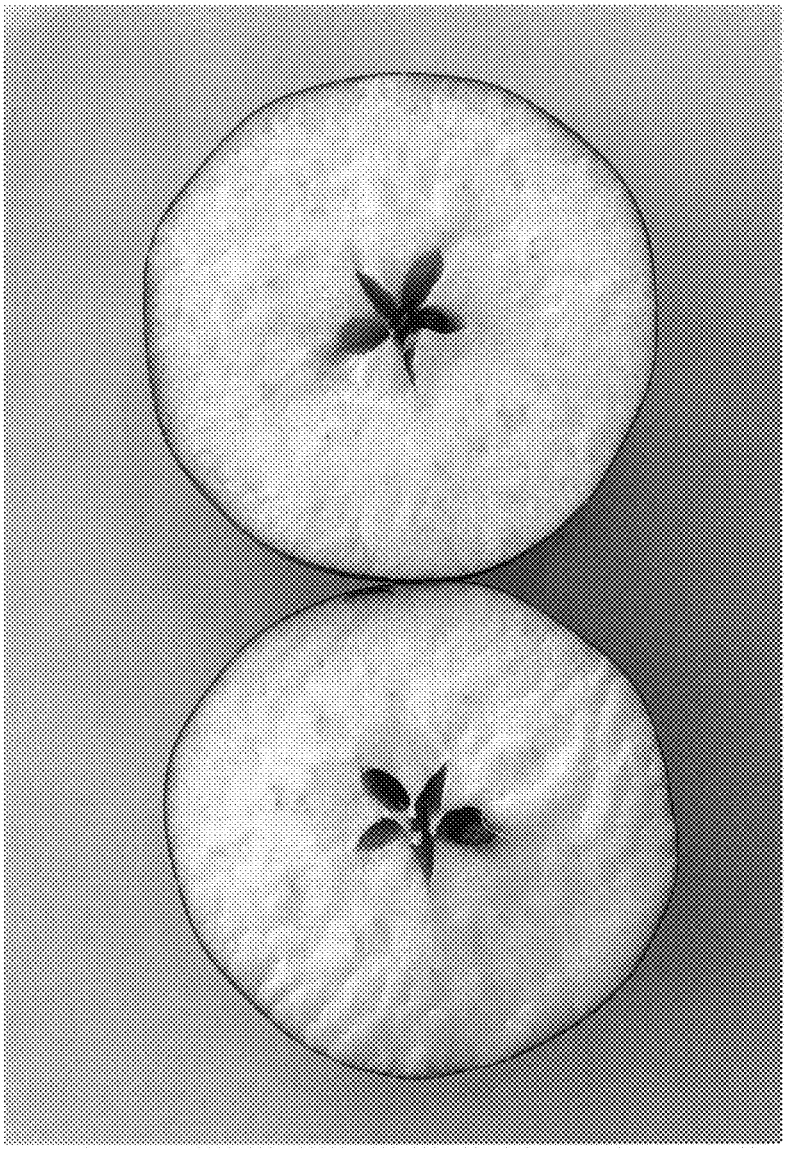
Figure 5:
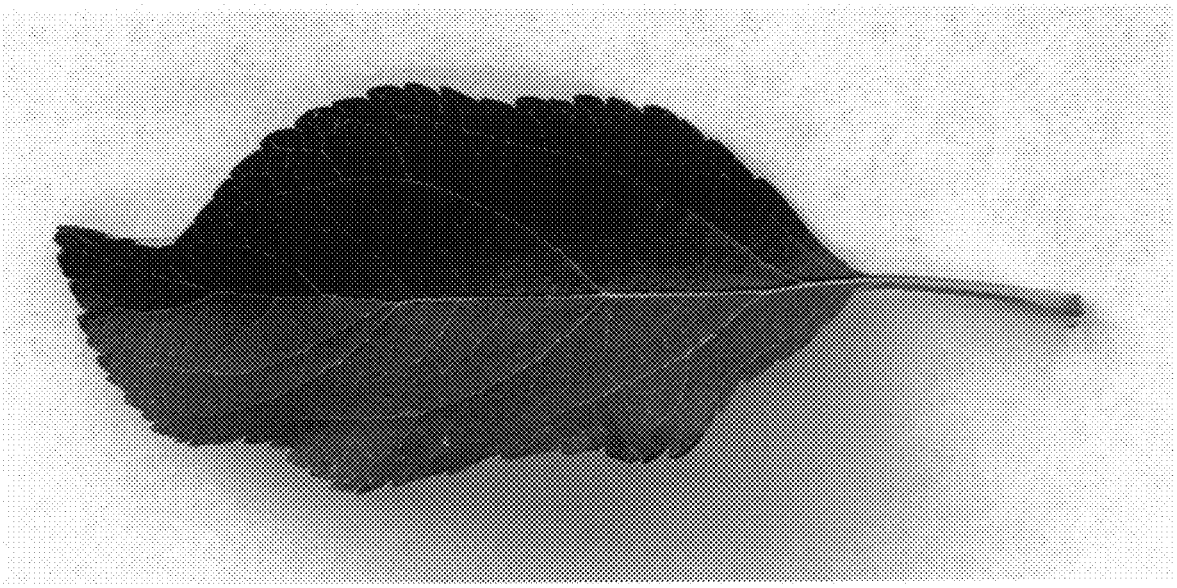
Figure 6:
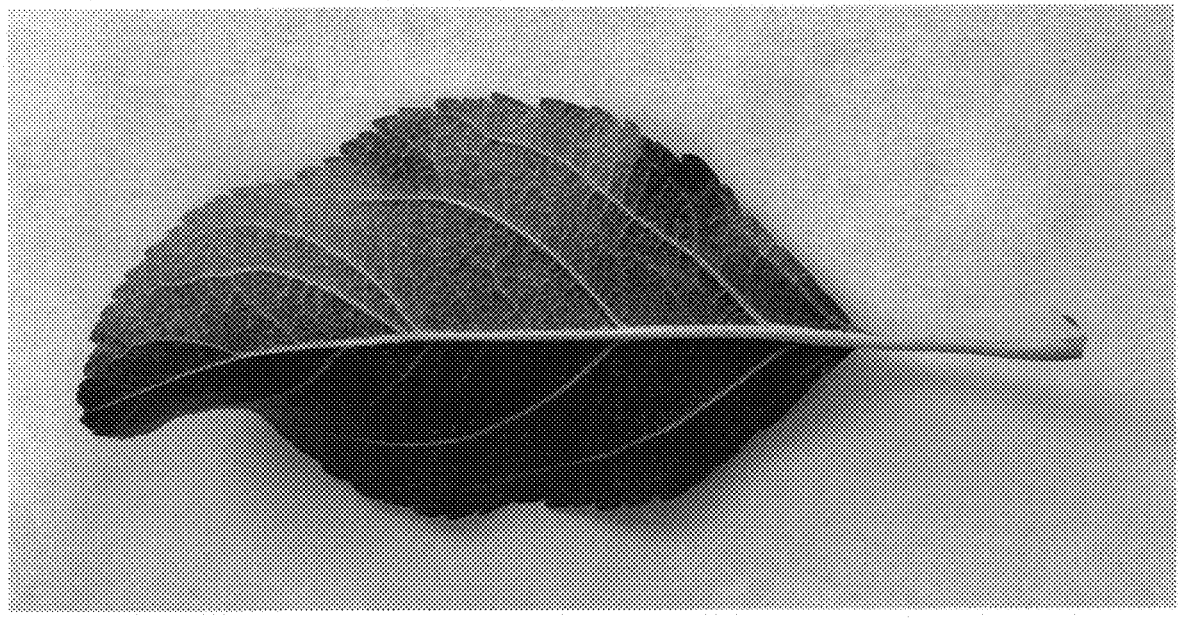
Figure 7:
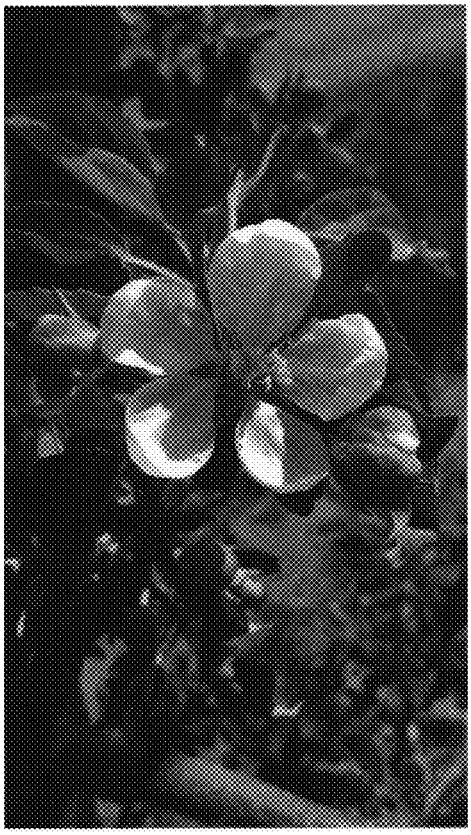

FIG. 1 is a side view of a 'Temptation' apple;
FIG. 2 is a top view of a 'Temptation' apple;
FIG. 3 is a bottom view of a 'Temptation' apple;
FIG. 4 shows the flesh, locules and seeds of a 'Temptation' apple;
FIG. 5 shows the upper surface of a leaf of a 'Temptation' apple tree;

FIG. 6 shows the lower surface of a leaf of a 'Temptation' apple tree; and,
FIG. 7 shows a blossom of a 'Temptation' apple tree.

DETAILED BOTANICAL DESCRIPTION OF THE VARIETY

The following-detailed botanical description is based primarily on observations made during the 2018 growing season near Basin City, Wash. The observed tree was planted in 2011 and grown on 'M.337' rootstock (not patented) in trellised high-density plantings. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Moderate (same as 'Foxtrot').
- *Type.*—Spur-type.
- *Habit.*—Upright.
- *Height.*—3.3 m.
- *Trunk diameter* (*at* 30 *cm above the graft*).—5 cm.
- *Bark texture.*—Smooth with prominent lenticels.
- *Bark color.*—Grey-brown N200C, N200D, with areas of Grey-brown 199B.
- *Trunk lenticels.*—About 5 to 10 per 5 $cm^2$; 8 mm long, 1 mm wide; white N155D.

Branch (fruiting branches located at around 1 m above the graft union):
- *Length.*—30 to 60 cm.
- *Diameter.*—2 to 3 cm.
- *Crotch angle.*—45 degrees to 90 degrees.
- *Bark color.*—Greyed-brown N200C, N200D.

One year old shoot:
*Length.*—30 cm.
*Color.*—Grey-brown N199A, N199B.
*Pubescence.*—Moderate (same as 'Foxtrot').
*Thickness.*—5 to 6 mm.
*Internode length.*—4 cm.
*Lenticels.*—4 to 6 per $cm^2$; round, 0.8 mm diameter; white N155D.

Flower buds:
*Quantity per spur.*—5.
*Shape.*—Pointed.
*Length.*—5 mm.
*Diameter.*—5 mm.
*Color* (*at time of bud burst, prior to opening*).—Red-purple N57A.

Flowers:
*Diameter of fully open flower.*—6 cm.
*Depth of fully open flower.*—<1 cm.
*Relative position of petal margins.*—Touching to free when fully open.
*Number per cluster.*—5.
*Date of first bloom* (2018).—April 21.
*Date of full bloom* (2018).—April 25.
*Pollinator.*—Required.

Petals:
*Number per flower.*—5 to 6.
*Shape.*—Orbicular.
*Length.*—3 cm.
*Width.*—1.5 cm.
*Apex.*—Obtuse.
*Base.*—Aequilateral.
*Margin.*—Entire, cupped.
*Color of upper surface.*—White NN155D to red-purple 65D, with tinges of red-purple N66C.
*Color of lower surface.*—White NN155D to red-purple 65D, with tinges of red-purple N66C.

Pistils:
*Length.*—10 mm to 13 mm.
*Stigma color.*—Yellow 11C.
*Style color.*—Yellow-green 145D.
*Ovary color.*—Yellow-green 145D.

Stamen:
*Quantity.*—18 to 20.
*Length.*—7 mm to 10 mm.
*Anther color.*—Yellow 11D.
*Filament color.*—White NN155C.
*Pollen.*—Scant; yellow 11D.

Pedicel:
*Length.*—20 mm to 30 mm.
*Diameter.*—2 mm to 3 mm.
*Color.*—Yellow-green 144D.

Sepals:
*Quantity.*—5.
*Width.*—2 mm to 3 mm at base.
*Shape.*—Triangular; apex acuminate.
*Margin.*—Entire.
*Color.*—Yellow-green 145A, pubescent.

Leaves:
*Shape.*—Ovate.
*Length.*—11 cm.
*Width.*—6 cm.
*Blade margin.*—Serrate.
*Apex.*—Acuminate.
*Base shape.*—Aequilateral, oblique.
*Color of upper surface.*—Yellow-green 144A, Green N137A.
*Color of lower surface.*—Yellow-green 147B, 147C.
*Leaf arrangement.*—Alternating.
*Attitude in relation to shoot.*—Upward.

Petiole:
*Length.*—3 to 3.5 cm.
*Diameter.*—2 to 3 mm.
*Color.*—Yellow-green 144D with some red purple 60B anthocyanincoloration at base.

Fruit:
*Quantity per cluster.*—One.
*Diameter.*—8 cm.
*Height.*—8 cm.
*Weight.*—225 g.
*Ratio of height to width.*—Equal.
*General shape in profile.*—Conic to globose.
*Position of maximum diameter.*—Equator.
*Ribbing.*—Minimal ribbing at calyx end.
*Crowning at calyx end.*—Present.
*Size of eye.*—5 mm to 9 mm.
*Aperture of eye.*—Closed to partly open.
*Length of sepal.*—4 mm to 5 mm.
*Bloom of skin.*—Absent or weak.
*Greasiness of skin.*—Absent or weak.
*Background color of skin.*—Yellow 7C.
*Amount of over color.*—Nearly 100%.
*Over color of skin.*—Red 53A, 53B.
*Intensity of over color.*—Very intense.
*Pattern of over color.*—Solid flush with weakly defined stripes.
*Amount of russet around stalk cavity.*—None.
*Amount of russet on cheeks.*—None.
*Area of russet around eye basin.*—None.
*Length of stalk.*—3 cm.
*Thickness of stalk.*—3 mm.
*Depth of stalk cavity.*—2.2 cm.
*Width of stalk cavity.*—4 cm.
*Depth of eye basin.*—1 cm.
*Width of eye basin.*—3 cm.
*Firmness of flesh.*—19 lbs. (at 5 days before harvest).
*Flesh texture.*—Crisp, fine.
*Aroma.*—Fragrant, floral.
*Juiciness.*—Juicy, similar to 'Foxtrot'.
*Brix.*—13.75 (at 5 days before harvest).
*Flesh color.*—Yellow 4D.
*Stem color.*—Greyed-orange 176C.

Seeds:
*Quantity per fruit.*—4 to 7.
*Shape.*—Teardrop shape.
*Size.*—8 mm long, 5 mm wide.
*Coloration.*—Greyed-orange 175A.

Harvest:
*Time for harvest.*—Late August, about 3 to 5 days prior to 'Foxtrot'.
*Number of picks.*—One.
*Harvest yield.*—35 tons per acre (based on high-density planting of 1100 trees per acre).
*Disease resistance/susceptibility.*—None noted.
*Market use.*—Fresh.

I claim:

1. A new and distinct apple tree substantially as described and illustrated herein.

* * * * *